(12) United States Patent
Rose et al.

(10) Patent No.: US 6,595,209 B1
(45) Date of Patent: *Jul. 22, 2003

(54) DRY POWDER DELIVERY SYSTEM

(76) Inventors: Jed E. Rose, 907 Kimball Dr., Durham, NC (US) 27705; Frederique Behm, 907 Kimball Dr., Durham, NC (US) 27705; James Turner, 14750 Ladd Rd., Atascosa, TX (US) 78002

( * ) Notice: Subject to any disclaimer, the term of this patent is extended or adjusted under 35 U.S.C. 154(b) by 0 days.

This patent is subject to a terminal disclaimer.

(21) Appl. No.: 09/016,262

(22) Filed: Jan. 30, 1998

Related U.S. Application Data

(63) Continuation of application No. 08/483,540, filed on Jun. 7, 1995, now Pat. No. 5,746,227, which is a continuation of application No. 08/014,773, filed on Feb. 8, 1993, now Pat. No. 5,441,060.

(51) Int. Cl.[7] .................. A61M 15/00; A61M 16/00; B05D 7/14; B65D 83/06
(52) U.S. Cl. .................. 128/203.15; 128/203.23; 128/203.24; 128/202.21; 137/270
(58) Field of Search ................ 131/270, 271, 131/347, 359; 128/203.15, 202.21, 203.23, 203.24, 205.21; 604/58

(56) References Cited

U.S. PATENT DOCUMENTS

| | | | | | |
|---|---|---|---|---|---|
| 390,455 | A | * | 10/1888 | Cleaveland | 128/203.15 |
| 2,142,353 | A | * | 1/1939 | Griffith | 128/203.12 |
| 2,513,145 | A | * | 6/1950 | Chapple | 131/273 |
| 2,603,215 | A | * | 7/1952 | Arnow | 131/273 |
| 2,642,063 | A | * | 6/1953 | Brown | 128/203.15 |
| 3,631,856 | A | * | 1/1972 | Taylor | 131/273 |
| 4,083,372 | A | * | 4/1978 | Boden | 131/8 |
| 4,284,089 | A | * | 8/1981 | Ray | 131/270 |
| 4,393,884 | A | * | 7/1983 | Jacobs | 131/273 |
| 4,765,348 | A | * | 8/1988 | Honeycutt | 131/273 |
| 4,892,109 | A | * | 1/1990 | Strubel | 131/194 |
| 4,969,476 | A | * | 11/1990 | Bale et al. | 131/336 |
| 5,050,621 | A | * | 9/1991 | Creighton et al. | 131/331 |
| 5,101,838 | A | * | 4/1992 | Schwartz et al. | 131/273 |
| 5,113,855 | A | * | 5/1992 | Newhouse | 128/203.12 |
| 5,167,242 | A | * | 12/1992 | Turner et al. | 131/273 |
| 5,284,163 | A | * | 2/1994 | Knudsen et al. | 131/270 |
| 5,287,850 | A | * | 2/1994 | Haber et al. | 128/203.21 |
| 5,441,060 | A | * | 8/1995 | Rose et al. | 131/271 |
| 5,687,746 | A | * | 11/1997 | Rose et al. | 131/273 |
| 5,746,227 | A | * | 5/1998 | Rose et al. | 131/270 |

* cited by examiner

*Primary Examiner*—John G. Weiss
*Assistant Examiner*—Joseph F. Weiss, Jr.

(57) ABSTRACT

A dry powder delivery system and method for use, the system having an elongated tube containing a matrix having a measured amount of dry particles of a therapeutic compound and a porous element having a desiccant therein. The porous element with the desiccant can be combined with the powder-containing matrix or it can be two separate elements. The pressure drop induced by inhalation of the user causes air to flow through the tube and into contact with the particles of dry powder for discharging the particles for inhalation by the user.

14 Claims, 3 Drawing Sheets

FIG.9
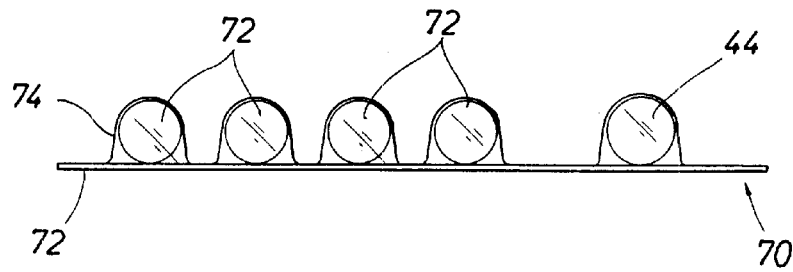
FIG.10
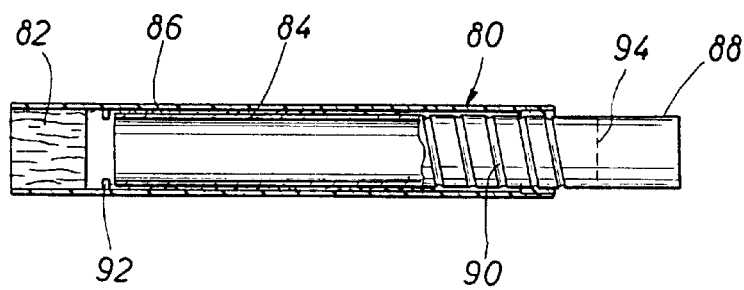
FIG.11
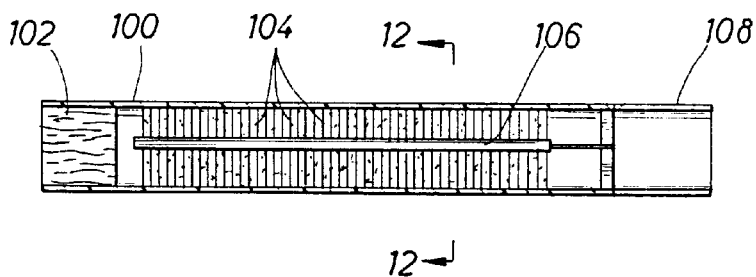
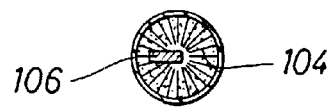
FIG.12

DRY POWDER DELIVERY SYSTEM

This is a continuation of application Ser. No. 08/483,540 filed Jun. 7, 1995 now U.S. Pat. No. 5,746,227, which is a continuation of application Ser. No. 08/014,773, filed Feb. 8, 1993, now U.S. Pat. No. 5,441,060.

FIELD OF THE INVENTION

The invention relates to a system for delivering a dry powder substance into the user's respiratory tract. The invention has particular applicability, but is not so limited, as a smoking cessation device where a nicotine compound, snuff, food acid or other smoking cessation aid, is delivered in dry powdered form from an oral inhalation device in the shape of an elongated tube.

BACKGROUND OF THE INVENTION

Evidence has linked many diseases such as heart disease and lung cancer to cigarette smoking. Each year, many deaths are caused by cigarette-related diseases. Indeed, excessive smoking is recognized as one of the major health problems throughout the world.

One reason it is extremely difficult for a smoker to quit is the addictive nature of nicotine. Even though nicotine is one of the risk factors in tobacco smoke, other substances formed during the combustion of tobacco, such as carbon monoxide, tar products, aldehydes and hydrocyanic acid, are considered by many to be a greater risk to the health of smokers.

In order to help smokers reduce or stop smoking altogether, acceptable alternatives have been provided to deliver nicotine in a form or manner other than by smoking. A number of products have been developed to accomplish this result. The first successful product used as a smoking substitute and/or smoking cessation aid was a chewing gum known as Nicorette® which contains nicotine as one of its active ingredients. See U.S. Pat. Nos. 3,877,486; 3,901,248; and 3,845,217.

Another product which has recently been marketed is a transdermal patch which includes a reservoir that holds nicotine base, as well as other drugs. When nicotine is transmitted through the skin into the user's bloodstream, it tends to alleviate a smoker's craving for nicotine. See U.S. Pat. Nos. 4,915,950 and 4,597,961. Nicotine nasal sprays have also been developed, both for use with a patch and independently. See U.S. Pat. Nos. 4,579,858 and 4,953,572.

All of these products have demonstrated some degree of success to the principles of nicotine replacement as an aid to smoking cessation, and that nicotine replacement can facilitate smoking cessation by providing some relief for certain withdrawal symptoms such as irritability and difficulty in concentrating. However, there still remains the subjective craving for cigarettes that is not effectively relieved by the pharmacologic effects of nicotine alone.

Some authorities have concluded that the sensations experienced in the upper and lower respiratory tracts, including the oral cavity upon inhalation of each puff of cigarette smoke, along with the taste and aroma of the smoke and the act of puffing, provide a considerable portion of the satisfaction experienced by a smoker. These sensory cues, in addition to the chemical dependency, are believed to help maintain a dependency on cigarettes which previously marketed products are unable to satisfy. Therefore, there is a need to develop smoking cessation aids which deliver the sensory and habitual aspects of smoking, in addition to the other substances found in cigarette smoke.

Many smoking cessation products have been developed, which simulate or closely approximate the look, feel, and taste of cigarettes for orally administering nicotine to the user. For example, attempts have been made to develop a smokeless cigarette where a heating element is used in combination with various types of carriers impregnated with nicotine base or nicotine in other forms. See, for example, U.S. Pat. Nos. 4,848,374; 4,892,109; 4,969,476; and 5,080,115.

Other attempts have been made to provide inhalers where nicotine base is stored in a reservoir mounted in a tubular housing, and aerosol droplets in an airstream or combined with a propellant are delivered orally. See, for example, U.S. Pat. Nos. 2,860,638; 4,284,089, 4,800,903 and 4,736,775.

These products have encountered various problems such as, for example, difficulty in providing a satisfactory shelf life, an inability to deliver sufficient amounts of nicotine directly into the lungs of the user and an unpleasant taste.

In addition to transmitting various nicotine compounds transdermally, nasally and orally, it has also been found that an aerosol in the form of a spray containing measured amounts of a food acid such as citric acid can be used to stem the craving for nicotine. Citric acid particles have been combined with a liquid carrier and administered alone or together with nicotine transdermally or with small amounts of tobacco smoke, to help in a smoking cessation program. See U.S. Pat. No. 4,715,387.

Attention has also been directed to delivering nicotine and other therapeutic compounds through the mouth in the form of a dry powder. It has been reported that in order to deliver a powder directly into the lower respiratory regions the powder should have a particle size of less than $5\mu$. Further, powders in the $5-10\mu$ range have been found not to penetrate as deeply and instead tend to stimulate the higher respiratory tract regions. See U.S. Pat. No. 4,635,651.

Because particles of these small sizes tend to agglomerate or form lumps, especially when exposed to moisture, the powders must be maintained in a dry state or the lumps broken up before they are delivered. Several devices have been developed where the powder is maintained in a capsule which has to be broken or punctured before the powder is delivered. See, for example, U.S. Pat. Nos. 3,858,582; 3,888,253; 3,991,762; 3,973,566; 4,338,931; and 5,070,870. These devices tend to be bulky or expensive to manufacture because they must provide a mechanism for breaking the capsule and metering the amount of powder to be delivered.

Other devices have been developed where dry powder is maintained in a chamber and metered doses are administered by rotating or moving various parts (U.S. Pat. No. 4,570,630; EPO 0 407 028 A2; GB 2,041,763; PCT WO 91/02558), or dry powder is carried in a web of material and the powder is removed by impact, brushing, or air current (PCT WO 90/13327; WO 92/00115). These devices all involve relatively complicated mechanical structures that are expensive to manufacture and cannot be incorporated into an elongated tubular holder.

Several other devices have been suggested where a single dose of powder is packaged in a container, but there is no provision for a multi-dose application or prevention of particle agglomeration. See, for example, U.S. Pat. Nos. 4,265,236; EPO 0 404 454.

Most of the dry powder devices are designed primarily to deliver measured amounts of powder directly into the lungs by providing a very low pressure drop across the chamber in which the powder is charged. While this action is satisfactory for asthma and other congestive ailments, it is much different from that of a smoker where a cloud of particles is drawn first into the mouth and then into the lungs. The action of a cigarette is more closely approximated by a much greater pressure drop in the inhaler device.

Thus, there is a need for an elongated container which can be used to deliver properly-sized dry particles of a therapeutic compound which prevents the particles from agglomerating, is relatively inexpensive to manufacture with a minimal number of components, and can closely approximate the drawing action of a smoker.

SUMMARY OF THE INVENTION

In order to solve the problems discussed above, the invention is directed to an oral inhalation device in the shape of an elongated tube, which can deliver a measured amount of a therapeutic compound in the form of a dry powder. By controlling the pressure drop of air flowing through the inhaler, the dry powder pulled into the mouth of the user closely approximates the bolus effect the smoker experiences when using a cigarette.

The particles arc preferably small enough so that a majority of the powder will not be deposited in the mouth or the upper respiratory tract, but is drawn for deposition in the lower respiratory tract and then into the blood stream. By having the particles less than 5$\mu$ in diameter, most of the particles may be deposited in the lower respiratory tract. If the action of the therapeutic compound is such that it is absorbed into the blood stream effectively through contact with surfaces in the upper respiratory tract, the particles could be sized in the 5–10$\mu$ range or greater.

The device is in the form of an elongated tube, for example, about 8 millimeters in diameter and about 60 millimeters long. The tube is formed of a moderately flexible polymer such as polyethylene or polypropylene with openings at both ends.

In one embodiment, the tube has a porous element which contains a desiccant through which air initially flows. The desiccant serves a two-fold purpose. First, it maintains particles in the tube free of moisture when the inhaler is stored and packaged in a moisture/oxygen impermeable wrapping such as a polyethylene or polyvinyl chloride (PCV) laminate. Secondly, it removes moisture from the incoming air stream. In this way, the air stream is dry when it contacts the dry particles so they will not stick together or bind to the matrix in which they are impregnated or to a screen or filter if one is used.

A matrix, positioned downstream from the porous element, contains a measured amount of dry particles of the therapeutic compound. The matrix is charged with particles which are preferably in the 5$\mu$ range, although larger particles can be used if desired. An advantage of utilizing a matrix for holding the particles is that agglomeration of the particles is avoided and the pressure drop across the inhaler is closely controlled. Alternatively, the porous element containing a desiccant could be combined with the powder-containing matrix, instead of providing two separate components.

A mouth piece is located downstream from the matrix. A suction is created by the user for drawing air through the porous element and matrix so that a measured amount of dry particulate matter is pulled into the mouth and then into the lower respiratory tract of the user. A desiccant can also be incorporated into the mouthpiece to absorb moisture from the user's lips.

The relative pressure drop across the porous element containing the desiccant and the matrix material should be adjusted to maximize the drying effect of the desiccant and the release of the dry particles into the air stream. In this way, air first moves through the porous element and is dried, and then through the matrix, pulling dry particles into the air stream and into the mouth of the user. The design of the mouthpiece could also be varied to regulate the pressure drop across the device.

If nicotine is the therapeutic compound used, the inhaler can be designed for 10 puffs, delivering about 100 micrograms of nicotine per puff, which can approximate the amount of nicotine delivered by a cigarette. In this way, a total of about 1 milligram of nicotine would be delivered to the user. As can be appreciated, the number of puffs can be regulated as well as the amount of nicotine in order to provide greater or lesser doses of nicotine per inhaler. In one embodiment, a series of inhalers can be provided with greater doses for smokers who are beginning a cessation program, are lesser doses as the user gradually weans himself or herself from the nicotine addiction.

The dry particles of nicotine salt can be formed by mixing substances such as tartaric acid or palmitic acid with nicotine base to form a nicotine salt and grinding the resulting solid compound into an appropriately sized powder. Palmitic acid is preferred because it is a naturally occurring substance in the human body, which may operate to buffer the nicotine and reduce the tendency of nicotine to irritate the mucus membranes and bronchial passageways. Dry powders formed of other compounds that can be therapeutic under certain conditions, for example snuff and food acids such as citric acid, could also be used.

The dry powder delivery device can be formed with separate cartridges containing the porous element and particle-impregnated matrix, and a separate mouth piece. A consumer package can be formed with a number of cartridges, for example, and one or more mouth pieces.

In another embodiment of the invention, a porous element containing a desiccant is formed in the distal or outer end of the device as described above. A measured amount of dry powder is placed between the tube that forms the housing and an inner tube that is rotatable relative to the housing. These tubes provide a metering mechanism for controlling the amount of powder delivered to the user. The inner and outer tubes can be provided with suitable openings or the inner tube can be moved to expose a measured amount of powder to the chamber each time the tubes are turned relative to each other. Brushes or bristles could also be used to hold the dry powder, with a scraper for dislodging the particles into the flow path.

The dry powder delivery system described above has distinct advantages over other attempts to provide a delivery system in an elongated tube. Metered doses can be delivered with few or no moving parts. The powder is maintained in a dry state and air passing through the powder is dried so that agglomeration is prevented.

The device described represents a marked improvement over inhalers which contain nicotine base to be delivered as a vapor. When the device of the present invention is used for a smoking cessation product, stability of nicotine in powder form allows more efficient delivery than possible with nicotine base. More importantly, dosage delivery when a powder is used is not affected by variations in temperature as with inhalers which utilize the more volatile nicotine base. Content uniformity of the powder is also much easier to control during the loading process. Further, greater amounts of nicotine can more tolerably be delivered per puff than possible with a nicotine base product.

BRIEF DESCRIPTION OF THE DRAWINGS

A better understanding of the invention can be obtained when the detailed description of exemplary embodiments set forth below is considered in conjunction with the appended drawings, in which.

FIG. 5 is a side sectional view showing the assembled device when the elements of FIGS. 3 and 4 are combined;

FIG. 6 is a front plan view of the distal end of the device, looking along site line 6—6 of FIG. 3;

FIG. 7 is a front plan view of the proximal end of the device, looking along site line 7—7 of FIG. 4;

FIG. 8 is a top plan view of a blister pack for consumer use in which a number of cartridges of FIG. 3 and a mouth piece of FIG. 4 are packaged;

FIG. 9 is a side plan view of the blister pack of FIG. 8;

FIG. 10 is a side sectional view of a second preferred embodiment of the dry powder delivery device;

FIG. 11 is a side sectional view of a third preferred embodiment of the dry powder delivery system; and FIG. 12 is a sectional view looking along the section line 12—12 of FIG. 11.

DETAILED DESCRIPTION OF EXEMPLARY EMBODIMENTS

Referring to FIG. 1, an early prototype delivery device is shown where a hollow tubular housing 10 is combined with a mouthpiece 12 which can be rotated relative to the housing 10 as discussed below. The housing 10 is hollow and filled with a dry powder 14 . The outer or distal end of the housing 10 has at least one air inlet 16 and a pair of air inlets 18 spaced around the distal end. The number and location of inlets can be varied depending on the characteristics of the powder 14 and the amount of air desired to be introduced into the housing.

A screen or mesh 20 is mounted in the housing 10 downstream from the dry powder 14 for delivering correctly sized particles when the user is creating a suction on the mouthpiece 12. The amount of suction can be adjusted by making the mouthpiece 12 rotatably adjustable relative to the housing 10 and providing a supplemental air opening 22 in the tubular housing 10 and a cooperating air opening 24 in the mouthpiece 12. The mouthpiece 12 can thus be rotated to regulate the amount of air drawn through the openings 22 and 24 by regulating the composite opening formed between the two openings.

The device of FIG. 1 was used in a pilot project to determine the efficacy of various dry powder therapeutic compounds for smoking cessation use. In various experiments with the device of FIG. 1, favorable results were reported of smoking satisfaction and the reduction in craving for cigarettes where citric acid, ascorbic acid, tobacco snuff and nicotine salts were used in dry powder form. In these cases, the powder had an average size in the range of about 20$\mu$ and the screen or baffle 20 had 40–120$\mu$ size openings.

In one series of tests, nicotine base was mixed with tartaric acid to form nicotine bitartrate salt. In this test, 1.622 grams of nicotine base (0.01 moles) was mixed with 3.02 grams of tartaric acid (0.02 moles). After mixing to form nicotine bitartrate, the material was ground using a mortar and pestle and then mixed with 27.816 grams of lactose powder. The resulting mixture was 5% nicotine by weight. Approximately 100 milligrams of powder was added to an empty delivery device such as shown in FIG. 1 for puffing by a subject.

Eight smokers were tested. The mean age was 44 years. They had been smoking a mean of 20 years. They reported smoking an average of slightly more than one pack per day, which yielded according to the Federal Trade Commission Guidelines, about. 98 milligrams of nicotine. In thirteen test sessions, the subjects puffed on the delivery device loaded with nicotine bitartrate either using lactose or cyclodextrin or maltodextrin as carriers. In either lactose or the two other carriers, different nicotine concentrations ranging from 1–5% were used. Ten puffs were taken for each rating. The following chart shows the nicotine deliveries which were calculated by weighing the device both before and after ten puffs:

| Session | % nicotine | mg nicotine delivered to mouth |
|---|---|---|
| 1 | 1% | — |
| 2 | 2% | — |
| 3 | 2% | — |
| 4 | 2% | — |
| 5 | 2% | — |
| 6 | 3.5% | 0.20 mg |
| 7 | 3.5% | 0.14 mg |
| 8 | 3.5% | 0.21 mg |
| 9 | 5% | 1.82 mg |
| 10 | 5% | 0.11 mg |
| 11 | 5% | — |
| 12 | 5% | 2.51 mg |
| 13 | 5% | 4.16 mg |

The particle size of the dry powder was analyzed using a cascade impactor. The mass median diameter, which was the diameter for which 50% of the mass was conveyed in larger particles and 50% in smaller particles, was roughly 5$\mu$. However, 32.2 milligrams of a total delivery of 47.2 milligrams consisted of larger particles that impacted on the cap of the impactor. Thus, the mass median diameter of the total powder aerosol delivery was actually greater than 12$\mu$, with 10% of the total material delivered being under 5$\mu$ in size.

These tests showed that larger doses of nicotine in a dry powder salt using ambient air technology can be delivered than in a comparable vapor delivery system. For example, a mean of 1.3 mg. of nicotine was delivered in 10 puffs in the prototype of FIG. 1, based on data from seven test sessions. This level represented more than 10 times the amount delivered by existing nicotine vapor inhaler technology. The sensory perceptions reported by the subjects also indicated a significant level of smoking satisfaction.

A second prototype of a dry delivery device is shown in FIG. 2 where a filter element 28 is mounted at the distal end of the tubular housing 10, which solved the problem of the dry powder 14 falling out of the openings 16 and 18 as shown in FIG. 1. The filter element 28 is formed of cellulose acetate and is the type used as a filter element in a cigarette. It also provided for a pressure drop across the element in order to simulate the draw pressure of a normal cigarette.

Because, in the prototype of FIG. 1, the powder 14 tended to stick on the screen 20, an elongated tubular screen member 30 was provided in place of the screen 20, which had openings of about 40–1μ in size. An air stream depicted by the arrows in FIG. 2, traveled through the openings when the user created a suction on the mouthpiece end 32. The device of FIG. 2 was used with several subjects, it was shown that it effectively allowed the subject to inhale a dry powder which was contained inside the tube 10 using ambient air instead of a propellant as used in many prior art devices.

Figure 1:
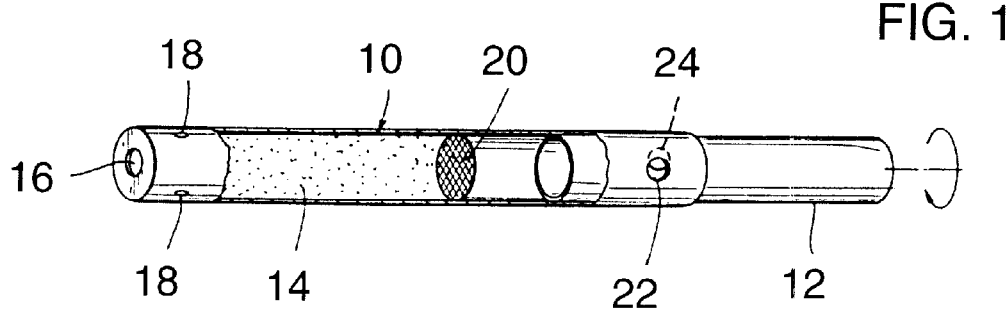
FIG. 1 is a side sectional view of an initial prototype of a dry powder delivery device.
Figure 2:
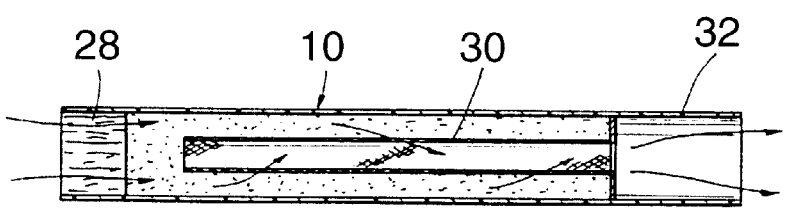
FIG. 2 is a side sectional view of a second initial prototype of a dry powder delivery device.
Figure 3:
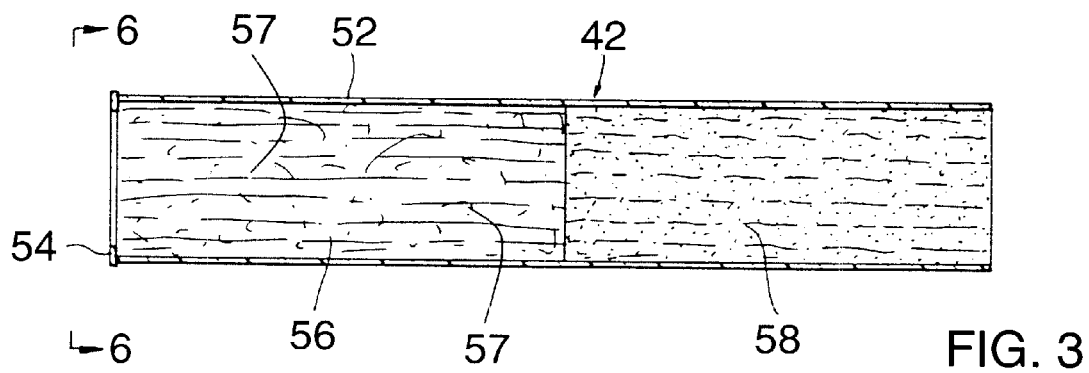
FIG. 3 is a side sectional view of one preferred embodiment of the dry powder delivery device where a cartridge includes a porous element containing a desiccant and a matrix filled with a dry medicament powder.

The device of FIG. 2 was used with four subjects who also wore transdermal patches containing nicotine base. The powder 14 was a compound containing citric acid in an amount of 50% by weight in lactose as a carrier. An amount of 100 mg. was placed in each device, which allowed the subject to take between 50–100 puffs per device.

The combination of a patch and inhaler of FIG. 2 resulted in the subjects reporting that there was a stronger sensation in the back of the mouth/throat and mixed reports of a sensation on the tongue and on the nose, windpipe and chest. Subjects reported that the combination of patch and citric acid delivered by the device of FIG. 2 was moderately helpful in relieving craving for cigarettes.

Additional tests were conducted to determine the extent and rapidity with which nicotine was absorbed from the respiratory tract of three cigarette smoking subjects, where a mean particle size smaller than that tested before was used. A jet mill micronizer manufactured by Sturtevant, Inc., Boston, Massachusetts, was used to grind particles of a nicotine salt to a mean size of less than 5μ, with a mass median diameter of 3–4μ. About 60–80% of the particles were less than or equal to 5μ in size.

The dry powder consisted of mixtures of both tartaric acid and nicotine base and palmitic acid and nicotine base. With palmitic acid, the acid was melted and nicotine base added and stirred. After the compound was cooled to room temperature, the resulting solid was broken by hand. In both cases, a 5% nicotine mixture resulted, which was ground in the jet mill micronizer to the particle size mentioned above, which resulted in a smoke-like powder.

The powder was delivered from the jet mill micronizer into a two liter breathing bag until enough powder totalling 0.065 mg. of nicotine was in each bag. Each patient inhaled from ten bags. About 70–80% of the powder in each bag was inhaled, resulting in a total delivery of about 0.45–0.52 mg. to each subject. The subjective ratings by the subjects indicated that the inhalations were perceived as fairly mild by two of the three subjects and a higher dose could have been tolerated by them. Blood samples were collected from each patient.

All three subjects showed increases in heart rate immediately after the inhalations of approximately 10 beats per minute, which suggested a nicotine absorption into the bloodstream. All of the subjects remarked that they perceived a nicotine effect in terms of reduction of the urge of smoke. Blood sample results clearly showed that substantial nicotine was delivered to the respiratory tract, as was suggested from the heart rate data. The mean peak plasma nicotine level achieved in the four tests was 22 ng/ml (s.d.=7.7). The mean time to reach the peak level was 12 minutes (s.d.=9.3). In all four cases a plasma nicotine level of at least 15 ng/ml had been achieved within the ten minute smoking period. This shows that nicotine was rapidly absorbed from the dry powder aerosol in an amount sufficient to produce plasma levels equivalent to those achieved by cigarette smoking.

These tests showed that a pharmaceutically significant dose of nicotine can be inhaled in dry salt form having a particle size of less than 5μ and that those inhalations were well tolerated from the standpoint of irritation. Moreover, the inhalations produced rapid physiological and subjective effects comparable to actual cigarette smoking.

Referring to FIGS. 3–7, a first preferred embodiment of the invention is illustrated where a delivery device (FIG. 3) is formed of two elements, a cartridge 42 (FIG. 3) and a mouthpiece 44 (FIG. 4) While this embodiment is described as formed of these two elements, it is apparent that the device 40 can be formed in a single unit with the same internal components.

Figure 6:
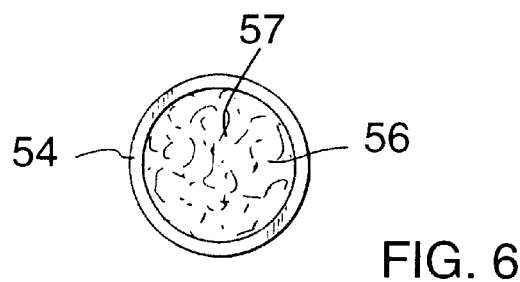
Figure 5:
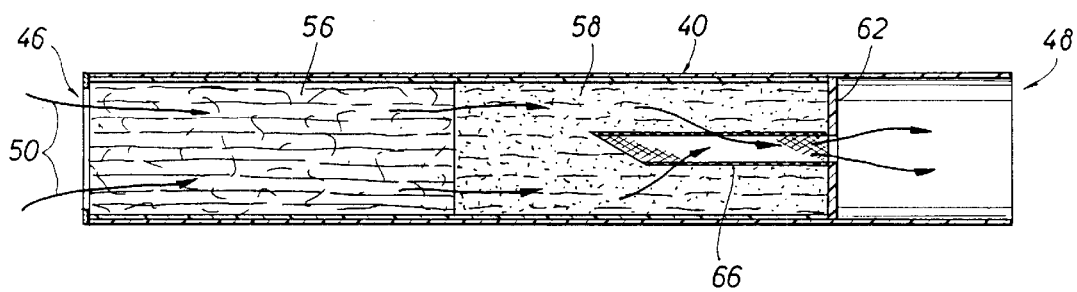

As shown best in FIGS. 5 and 6 the device 40 has a distal end 46 through which air is introduced, and a proximal end 48 which is placed in the mouth of the user who, when creating a suction, causes air to flow through the inhaler as illustrated by arrows 50. The cartridge 42 includes housing 52 with an open ridged end piece 54.

A porous element 56 is mounted in the housing 52 on the downstream side of the end piece 54 and contains a desiccant 57 such as, for example, anhydrous calcium sulfate particles. In a preferred embodiment, the porous element 56 is formed of a porous polyethylene with a multitude of irregular passageways that extend from one end to the other, with the desiccant 57 being impregnated in the polymer matrix and exposed to air flowing through the passageways. Alternatively, the porous element 56 can be formed of polyethylene fibers with a granular desiccant 57 either dispersed throughout or impregnated in the fibers.

A matrix 58 is mounted on the downstream side of the porous element 56, and contains a measured amount of dry powder therapeutic compound. The matrix 58 is formed of a filter rod made up of polymer fibers, preferably polyethylene, which have the dry powder dispersed throughout the fiber matrix. Alternatively, the matrix 58 could be formed with desiccant impregnated in the filter, thereby eliminating the need for porous element 56.

Figure 4:
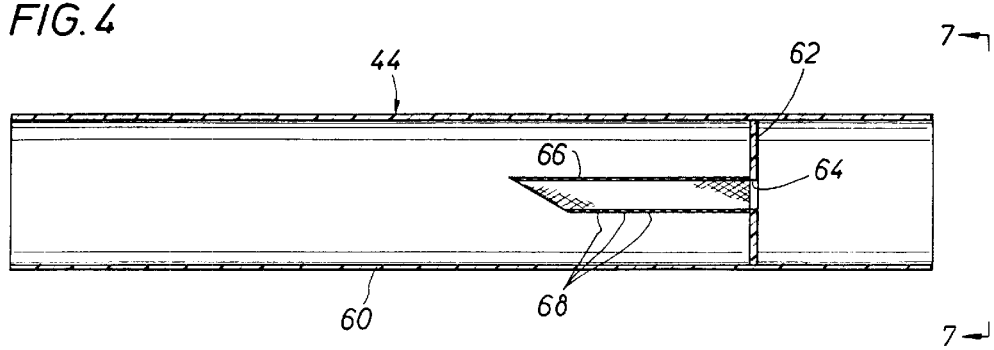
FIG. 4 is a side sectional view of a mouth piece which is designed to be combined with the cartridge of FIG. 3.
Figure 7:
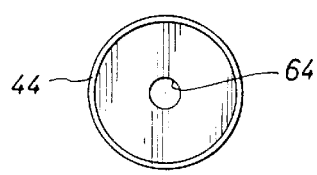
Figure 8:
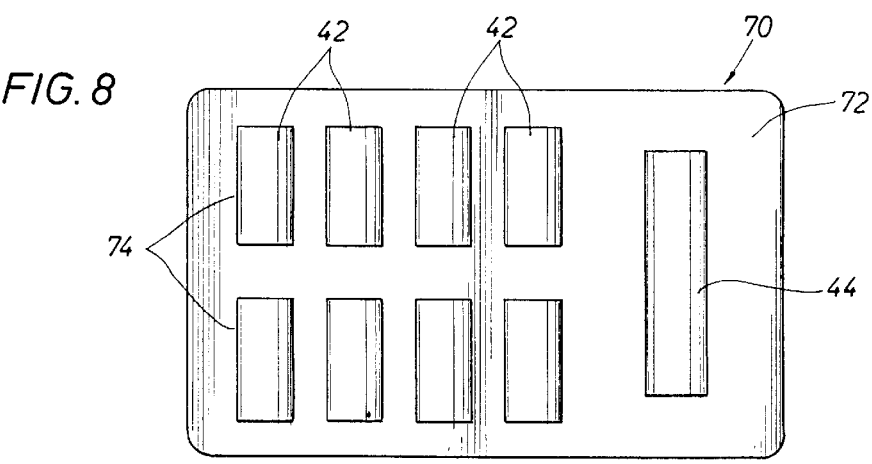

As shown in FIGS. 4 and 7 the mouthpiece 44 includes a tubular housing 62 formed of a length of a flexible polymer such as, for example, polyethylene or polypropylene. The housing 60 includes a recessed end piece 62 with a central aperture 64 through which air can be drawn after it passes through the elements of the cartridge 42.

An elongated screen element 66 is mounted on and projects from the distal side of the end piece 62 so that when the inhaler is assembled as shown in FIG. 5, the screen element 66 is embedded in the matrix 58. The screen element 66 includes a network of openings 68 through which air and particles can flow when the user creates a pressure drop on the mouthpiece 44 by drawing on it. Preferably, the openings 68 are at least 10μ in diameter when particles 5μ in diameter and less are impregnated in the matrix 58. The openings can be adjusted to provide delivery of various sized particles.

The desiccant contained in the porous element 56 serves two purposes. First, when the cartridge is stored in a container with an oxygen/moisture proof wrapper, the desiccant operates to absorb any moisture in the container to prevent the particles embedded in the matrix 58 from agglomerating or sticking to the matrix material. Second, when the device 40 is assembled as shown in FIG. 5 and air is pulled through the various elements of the device, air first passes through the porous element so that it is dried to prevent any moisture from affecting dislodgement of the particles from the matrix 58 and their ability to flow in the direction of the arrows 50.

In practice, the device 10 as shown in FIG. 5 is about 60 mm long and 8 mm in diameter, to closely approximate the size of cigarette. The openings in the matrix 58 can be adjusted so that measured amounts of dry powder can be delivered to the user depending on the dose level and the number of puffs to be delivered. For example, one such device can be designed to deliver 10 puffs at 100 micrograms of nicotine per puff. In such a device, a preferred powder is formed by mixing palmitic acid and nicotine base to form a nicotine salt. Palmitic acid is melted at about 70° C. and nicotine base is added until there is a solution of 95% palmitic acid and 5% nicotine. The solution is cooled at room temperature and the resulting flaky solid is broken by hand. The pieces are reduced to about 5μ size by an air jet micronizer. Enough particles are charged in the matrix 58 to deliver about 1 mg. of nicotine, which at a 5% nicotine concentration would amount to about 20 mg.

With the powder size being about 5μ, the matrix should be formed of fibers about 0.2–1 mm in diameter with passageways of at least 8μ in diameter so the powder is loosely packed and will enter the air stream as it moves through the matrix. The openings 68 in the filter element 68 should be at least 10μ in diameter to allow the powder to move through the opening 64 in the wall 62.

In order to enhance the delivery of correctly-sized particles from the matrix 58, the particles could all be charged with either a negative or positive polarity in a known way, with the fibers having the opposite charge. Alternatively, the powder could be coated with a substance that resists sticking such as tricalcium phosphate. Also, spherical shaping of the particles could be achieved to reduce agglomeration.

When the device 40 is formed of a cartridge 42 and a mouth piece 44, they can be packaged for consumer sale as shown in FIGS. 8 and 9. For example, a blister pack 70 has a backing layer 72 of aluminum foil that is overlaid by a transparent blister sheet 74 formed of polyvinyl chloride or polyethylene which operates to encase a plurality of cartridges 42 and a mouth piece 44.

The aluminum foil backing 72 and polymer coating 74 operate as an effective oxygen-moisture barrier for the cartridges to prevent moisture from impregnating the dry particles in the matrix 58. The presence of the desiccant in the porous element will maintain the particles in a dry state when stored in the blister pack 70. When a consumer desires to assemble one of the inhalers 40, he or she simply peels back the polymer layer 74, exposing the mouth piece 44 and one of the cartridges 42 and then assembles them as shown in FIGS. 8 and 9.

Another embodiment of the invention is shown in FIG. 10 where an elongated tubular housing 80 is formed of a suitable polymer such as, for example, polyethylene or polypropylene. A porous element 82 is mounted in the distal end of the housing 80, which has a construction similar to the porous element 56 described in conjunction with FIGS. 3–7.

An inner sleeve 84 is mounted for rotation within the housing 80, with a measured amount of dry particulate powder charged in a space 86 formed between the housing 80 and the sleeve 84. A portion of the inner sleeve 84 extends beyond the proximal end of the housing 80 to form a mouthpiece 88. The housing 80 and inner sleeve 84 are formed with cooperating threads 90 so that the mouthpiece 88 can be turned relative to the housing 80 to release powder contained in the gap 86 as the inner sleeve moves away from a stop 92 that is mounted in the housing adjacent to the porous element 82.

In addition to releasing the dry powder, rotation of the inner sleeve 8μ also operates to grind the powder to break up any lumps that might have formed. The sizes of the tubes and pitch of the threads can be calibrated so that each one-quarter, one-half or full turn could deliver enough powder for one puff into the cavity formed inside the inner tube 84. A filter 94 can be mounted in the mouthpiece 88 to deliver correctly sized particles.

Another embodiment of the invention is shown schematically in FIG. 11, where a tubular housing 100 contains a porous element 102 which includes a desiccant such as described above for the embodiments in FIGS. 3–10. A series of bristles or brush elements 104 are mounted on the inner surface of the housing 100. A charge of a dry powder therapeutic compound is embedded in the bristles.

A scraper 106 is mounted on a mouthpiece 108 that is rotatable relative to the housing 100. The scraper 106 projects between the bristles in each brush element 104 so that when the mouthpiece 108 is rotated it causes the scraper 106 to scrape the bristles and dislodge the particles of dry powder.

If, for example, 10 puffs are desired, the device can be calibrated so that the scraper 106 dislodges enough powder for each puff through rotation of about 36°. When the user creates a suction on the mouthpiece after it is rotated an appropriate distance, the dislodged particles enter the air stream and are inhaled.

The devices described above effectively utilize an elongated tube with minimal or no moving parts to delivery measured amounts of a dry powder therapeutic compound through the same inhalation technique used by a smoker. The device can be calibrated and charged with appropriate doses, ranging from that in a typical cigarette to weaker doses for a gradual withdrawal program.

One with ordinary skill in the art will be able to make improvements and modifications to the invention without departing from the spirit and scope of the invention, all of which are contemplated as falling within the scope of the appended claims.

What is claimed is:

1. A dry powder delivery system comprising:

(a) an elongated tubular housing having proximal and distal ends and a passageway for air flow between the end, the housing being adapted to be connected to a mouth of a user;

(b) the distal end having at last one inlet opening through which air can be introduced into the passageway;

(c) the proximal end forming a mouth piece with at least one end outlet opening through which air can be withdrawn through the passageway;

(d) a resistance member that creates a controlled pressure drop between the distal and proximal ends and a resistance to the drawing of air through the mouth piece, said resistance being such that particles are drawn into the mouth of the user to simulate the action of puffing on a cigarette; and (e) a matrix with a plurality of passageways containing a dry powder being positioned in the flow path, for introducing an amount of particles of the dry powder compound having a therapeutic capability into the flow path in the passageway so that said particles will travel downstream from the resistance member whereby suction created at the proximal end causes air to flow in the passageway and into contact with particles of said dry powder for discharge through the outlet at a low velocity.

2. The dry powder delivery system of claim 1,where the particles are sized so the particles can be drawn into the user's mouth and inhaled.

3. A method for delivering dry powder particles through a device adapted to be connected to a mouth of a user, comprising the steps of:
   (a) providing an opening in a proximal end of an elongated housing for drawing air into a flow path in the housing, from an opening in a distal end of the housing, and through a resistance member in the housing for controlling pressure drop in the housing and for drawing of air into a user's mouth;
   (b) introducing an amount of dry powder particles having a therapeutic capability into the housing so that the particles will travel downstream from the resistance member in a non-agglomerated state, the dry powder particles being sized so that the particles can be drawn into the user's mouth and inhaled, the particles being contained within a plurality of passageways of a matrix positioned in the flow path.

4. The method of claim 3, wherein the particles are sized so that the particles are deposited in an oral cavity and upper respiratory tract of the user after being drawn into its mouth.

5. The method of claim 3, wherein the dry powder ranges from $5\mu$–$10\mu$ in size.

6. The method of claim 3, wherein the particles the dry powder comprises at least a nicotine salt.

7. The method of claim 3, wherein the dry powder comprises a nicotine salt formed of palmitic acid and nicotine base.

8. The method of claim 3, wherein the dry powder comprises at least powdered tobacco.

9. The method of claim 3, wherein the dry powder comprises at least citric acid.

10. The method of claim 3, wherein the elongated housing is a tube formed of a flexible polymer that is about 60 mm. long and 8 mm. in diameter.

11. The method of claim 3, wherein the proximal end comprises a recessed wall inside the housing.

12. The method of claim 3, wherein a desiccant is provided in the housing.

13. The method of claim 3, and including an elongated element projecting into the matrix.

14. The method of claim 3, wherein at least a substantial portion of the dry powder particles have a particle size less than $5\mu$ for also depositing the particles in a lower respiratory tract of the user.

* * * * *

UNITED STATES PATENT AND TRADEMARK OFFICE
CERTIFICATE OF CORRECTION

PATENT NO.     : 6,595,209 B1
DATED          : July 22, 2003
INVENTOR(S)    : Jed E. Rose et al.

It is certified that error appears in the above-identified patent and that said Letters Patent is hereby corrected as shown below:

<u>Column 1,</u>
Line 7, insert the following:
--                  U.S. GOVERNMENT RIGHTS
       This invention was made with Government support under Grant No. DA02665 awarded by the NIDA. The Government has certain rights in the invention. --

Signed and Sealed this

Second Day of March, 2004

JON W. DUDAS
*Acting Director of the United States Patent and Trademark Office*